United States Patent [19]

Marshall

[11] 4,205,680
[45] Jun. 3, 1980

[54] RADIOPAQUE LAPARATOMY SPONGE

[75] Inventor: Lyman R. Marshall, Asheville, N.C.

[73] Assignee: Work Wear Corporation, Inc., Cleveland, Ohio

[21] Appl. No.: 869,121

[22] Filed: Jan. 13, 1978

[51] Int. Cl.² .................. A61F 13/00; A61L 15/00
[52] U.S. Cl. ................................. 128/296; 128/156
[58] Field of Search .............. 128/296, 156, 1.1, 1.2

[56] References Cited

U.S. PATENT DOCUMENTS

| | | | |
|---|---|---|---|
| 2,972,350 | 2/1961 | Deker | 128/296 |
| 3,074,406 | 6/1963 | Numerof et al. | 128/296 |
| 3,587,583 | 6/1971 | Greenberg | 128/296 |
| 3,618,609 | 11/1971 | Glick | 128/296 |
| 3,630,202 | 12/1971 | Small | 128/296 |
| 3,698,393 | 10/1972 | Stone | 128/296 |
| 3,756,241 | 9/1973 | Patience | 128/296 |
| 3,837,950 | 9/1974 | Reimels | 156/73 |
| 3,911,922 | 10/1975 | Kliger | 128/296 |
| 3,941,132 | 3/1976 | Lenaghan | 128/296 |
| 3,948,390 | 4/1976 | Ferreri | 206/370 |
| 3,961,629 | 6/1976 | Richter et al. | 128/296 |
| 3,965,907 | 6/1976 | Hardy et al. | 128/296 |
| 3,971,381 | 7/1976 | Gibson | 128/296 |
| 3,977,406 | 8/1976 | Roth | 128/296 |
| 4,068,666 | 1/1978 | Shiff | 128/296 |

Primary Examiner—Robert W. Michell
Assistant Examiner—C. W. Shedd
Attorney, Agent, or Firm—Pearne, Gordon, Sessins, McCoy & Granger

[57] ABSTRACT

A medical sponge having a radiopaque handle for detection by radiation scanning techniques which is arranged to display a readily identifiable trace and which is adapted to reduce the chance of separation of radiopaque material from the sponge body.

12 Claims, 4 Drawing Figures

RADIOPAQUE LAPARATOMY SPONGE

BACKGROUND OF THE INVENTION

This invention relates to medical sponges having provision for radiopaque detection.

PRIOR ART

Medical sponges, by common practice, are provided with a substance which is detectable through some form of radiation in order to positively ascertain whether or not a sponge, despite precautionary measures and prescribed routines, has been inadvertently left in a surgical incision after completion of an operation. X-ray detectable materials are customarily used in such applications although other materials including radioactive and magnetic materials depending on different forms of radiation have been used and/or proposed. In many cases radiopaque materials have been carried in a flexible thermoplastic body of limited size with respect to the size of the sponge which element is secured by sewing or bonding on or in the sponge. U.S. Pat. Nos. 3,756,241, 3,837,950, 3,911,922, and 3,965,907, for example, disclose radiopaque indicator strips, fibers and other shapes heat bonded to medical sponges.

A problem encountered with prior X-ray detectable elements or indicators has been limited visibility and distinctiveness when viewed by scanning equipment making it difficult to locate such elements or discriminate them from the detected image of surrounding body tissue, or sutures. The difficulty in visually discriminating radiopaque elements from surrounding natural or implanted matter is often increased where the element has a regular geometric configuration. Moreover, planar elements having a distinctive profile can assume a spatial relationship with respect to the scanning equipment, causing it to be viewed edgewise, or nearly edgewise, whereby its characteristic shape is not displayed.

Use of a detectable magnetic element either in the body or handle of a medical sponge has been proposed in U.S. Pat. No. 3,587,583. Other proposed constructions have included stringing a succession of sponges on a common wire or strand such as shown in U.S. Pat. Nos. 3,630,202; 3,941,132.

With the use of at least some of the sponge designs of the prior art there is a danger that a radiopaque element or portion thereof may become dislodged from the sponge. The risk of such indicator dislodgement in the prior art depends upon many factors, including the service and treatment experienced by the sponge.

SUMMARY OF THE INVENTION

The invention provides a medical sponge having associated with a handle thereof a radiopaque indicator element. Upon use, the indicator is adapted to assume a characteristic convoluted, three-dimensional figure which when viewed or scanned by suitable equipment from any orientation, displays a sinuous pattern which is readily traced for visual identification. The pattern exhibited by the indicator element, by virtue of this curvature, is easily distinguishable from natural structural features or sutures within a body. The indicator element is adapted to assume a convoluted configuration as a result of its high degree of flexibility and its association with a flexible handle which is relatively free of restriction by the sponge when the latter is folded in a regular pattern. Moreover, the indicator element and handle have a combined structure which is adapted to flex in a plurality of planes with equal facility to ensure that the indicator element will assume the desired three dimensional or multi-plane configuration for positive visibility.

In the preferred embodiment the sponge is provided with a handle that is a free loop formed by attaching its ends at a common point to the sponge material. The looped handle configuration upon scanning gives the indicating element a positive and recognizable curvature while from the standpoint of actual primary use affords a convenient finger grip for manipulation of the sponge.

In the disclosed embodiment of the invention, the indicator element is encapsulated within a tightly braided seamless handle. In forming a sheath, the braided handle protects the indicator element against abrasion, snagging, and like harm and prevents separation of the indicator element or portions thereof from the sponge. The disclosed assembly is economical to manufacture since the indicator element may be laid into the handle as the latter is automatically fabricated on a machine so that the indicator element may be subsequently fixed to the sponge material simply with attachment of the handle. Economy of manufacture is of prime importance where a sponge is used only once or a very limited number of times.

DESCRIPTION OF THE PREFERRED EMBODIMENT

Figure 1:
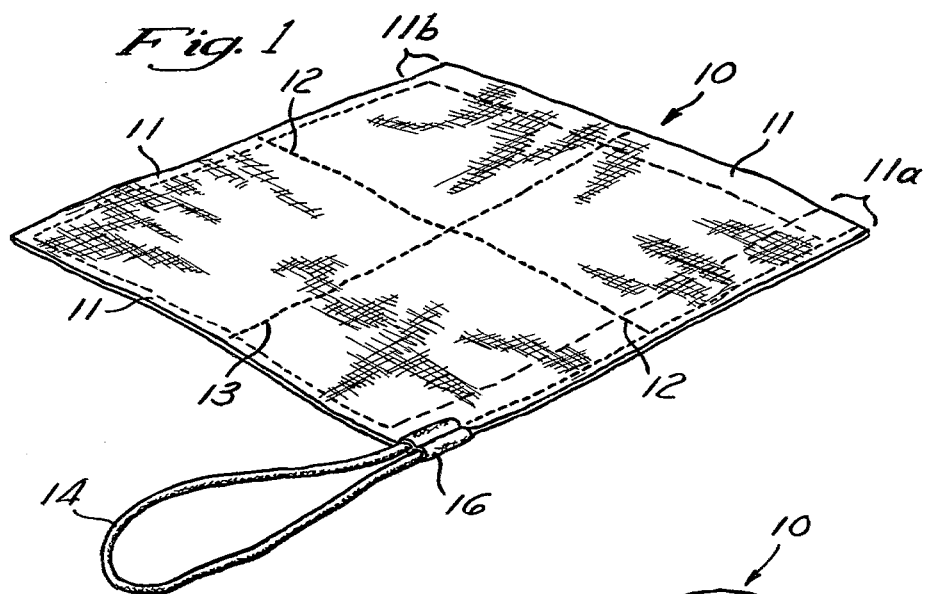
FIG. 1 is a perspective view of a medical sponge constructed in accordance with the invention.
Figure 2:
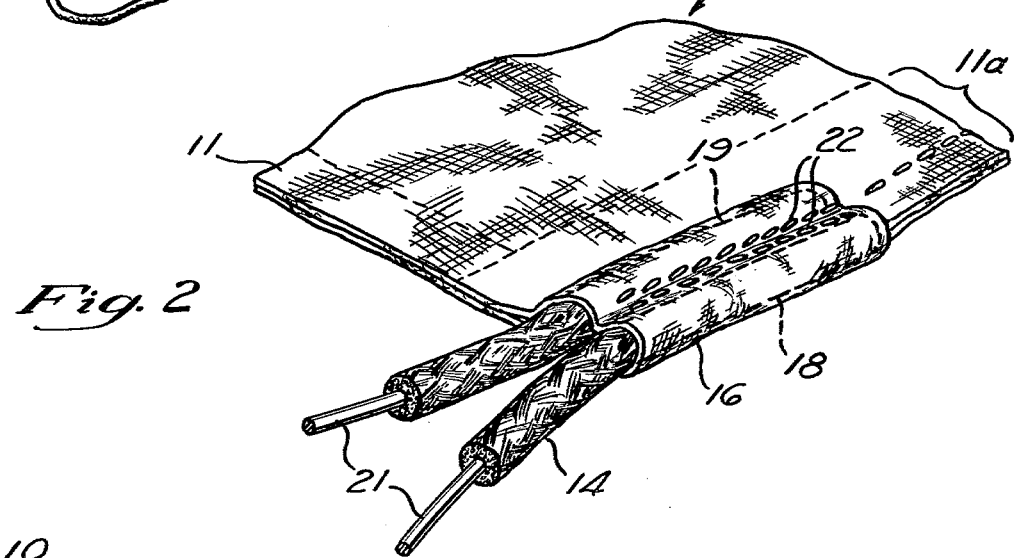
FIG. 2 is a perspective fragmentary view on an enlarged scale illustrating a manner of attachment of the handle to the sponge.

A medical sponge 10, typically used in laparotomy procedures, is constructed of multiple plies of intertwined and preferably loosely woven cotton threads or like material adapted to absorb animal body fluids in accordance with conventional practice. The plies of the sponge 10, which in the preferred embodiment are four in number, are stitched together with cotton thread or like material along a full peripheral hem 11 and across center lines at 12 and 13. In the example of FIG. 1, the sponge 10 is approximately 14 inches square. The hem of at least two abutting edges 11a, 11b in the preferred embodiment of the sponge is inturned and has twice the number of plies, namely eight, as that of the main area of the sponge. A handle 14 is attached to one corner 16 of the sponge 10 associated with one of the doubled fabric hem edges 11a.

Figure 3:
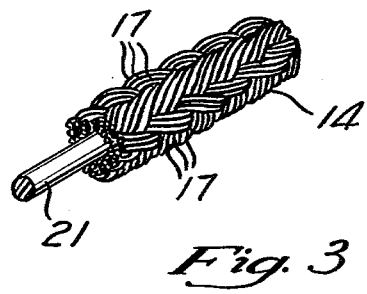
FIG. 3 is a perspective fragmentary view with still greater enlargement, showing constructional details of the handle and an indicator element.

The handle 14 is a generally round, seamless sleeve or tube fabricated by tightly braiding a plurality of cotton threads 17 or like absorbent fibers. As indicated in FIG. 3, the individual threads 17 on the handle 14 are tightly grouped and packed against one another so that substantially no radial gaps or holes exist in the wall of the handle. End portions 18, 19 of the handle 14 are tucked between and securely sewn to the doubled hem 11a at the corner 16. In the illustrated example, the handle 14 has a total length of approximately 18 inches, with the anchored end portions 18, 19 being each approximately one inch such that the major portion of the handle length is free of direct association with the body of the sponge 10. As indicated, the handle end portions 18, 19 are closely adjacent, and preferably abut one another while extending parallel to the longitudinal direction of the associated double hem 11a. The looped handle 14 provides a convenient and positive finger grip for manipulation and retrieval of the medical sponge 10 during use within and about a surgical incision or wound.

Disposed within and substantially coextensive in length with the handle 14 is an indicator element in the form of an elongated, flexible strand 21. The strand 21 has substantially greater radiopacity than that of the body of the sponge 10 to render the handle 14 radiopaque and to permit it to be located by medical scanning equipment. Where the scanning equipment utilizes X-rays, the strand or indicating element 21 may be formed of barium sulphate in an elastomeric, thermoplastic binder material known in the prior art. By way of example, the radiopaque strand 21 is round and has a diameter of approximately 0.025 to 0.030 inches. The term "radiopaque" as used herein is intended to cover materials which, when compared to a particular sponge material being used and normal animal body matter, are relatively opaque or reflective to other forms of radiation, beside X-ray radiation, such as sound radiation employed in ultrasonic scanners.

The indicator strand element 21 is conveniently formed as an extrusion and disposed in the handle by laying it as a continuous strand into the handle as the handle is being formed in a continuous process on an automatic braiding machine, in accordance with conventional braid-forming practices. Thereafter, the handle and indicator stock are cut to length and then simultaneously sewn to the sponge material, thereby avoiding separate handling and attachment of the handle and indicator element.

Figure 4:
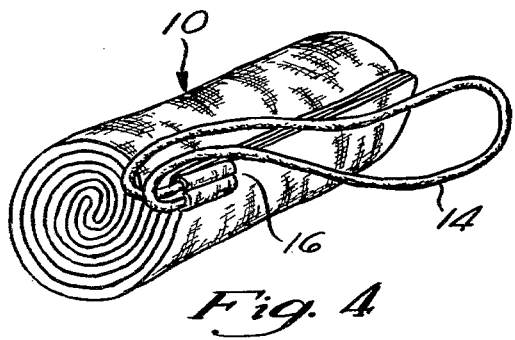
FIG. 4 is a perspective view of the sponge in a typical folded configuration with the handle substantially free of confinement by the sponge.

It is important that the radiopaque indicator element 21 yields a highly distinctive trace when scanned by radiation detection devices. The looped outline of the handle 14, high flexibility of the handle and indicator element, and manner of attachment of the handle all contribute to a natural tendency of the handle and indicator element to assume a convoluted multi-plane configuration restricted in use primarily only by surrounding body tissue. The contribution of the loop shape and high flexibility of the handle and indicator combination towards the assumption of a three-dimnensional figure are self-evident. It is to be noted that the round structure of both the handle and indicator element, as well as the central disposition of the indicator element in the handle, provides a combined section modulus which allows the combination to flex in a plurality of planes with equal facility. The attachment of the loop handle 14 to a common point in the doubled hem section 11a of the sponge results in a relatively stiff area at the corner 16, owing to the local bulk of the fabric there. Fabric stiffness at this anchor point, as demonstrated in FIG. 4, generally results in the immediately adjacent free area of the handle and indicator assuming a curvature of relatively smaller radius which is readily distinguished from more linear scanning traces commonly associated with bone or sutures which may have radiopaque characteristics.

The multi-plane or three-dimensional configuration assumed by the indicator element 21 greatly reduces the chance of a scanning device seeing only an edge view of a planar indicator element or a single reach of the looped indicator element.

The handle 14 forms a sheath for the indicator element 21 to protect it from physical damage through abrasion, snagging, cuts and the like. The essentially complete encapsulation of the indicator element 21 by the handle 14 likewise eliminates the possibility of dissociation of the indicator element, or a portion of it, from the body of the sponge. This encapsulation function is particularly important where the indicator element 21 is sucsceptible to embrittlement under repeated sterilization or other treatment used where the sponge is reused. Inspection of FIG. 3 illustrates that the indicator element 21 is relatively large in diameter as compared to the size of the threads 17 braided into the handle 14. With the threads tightly abutting each other in this handle structure, no radial path is available for escape of a broken end of the indicator element 21. Axial escape of the indicator element 21 through the handle ends 18, 19 is precluded by constriction of these handle areas by the associated stitches of cotton thread or like material indicated at 22, and a barrier provided by the double hem plies between which the handle ends are inserted.

Although a preferred embodiment of this invention is illustrated, it should be understood that various modifications and rearrangements of parts may be resorted to without departing from the scope of the invention disclosed and claimed herein.

What is claimed is:

1. A medical sponge comprising a mass of absorbent material for absorbing body fluid, a flexible tubular handle of cotton or like material secured to and extending free of the absorbent material, the handle being adapted to be gripped to permit manual manipulation of the sponge within or about a surgical incision, as well as retrieval of the sponge from such incision, and an elongated continuous strand of indicating material distinct from, but within and substantially completely encapsulated by the tubular handle, said indicating material being substantially more radiopaque than the absorbent sponge material and being sufficiently radiopaque to be detected and distinguished from an animal body by radiation scanning techniques, the tubular handle being formed by a wall constructed and arranged to contain the strand therein and effectively prevent escape of the strand or portion thereof from the handle along a radial path, means associated with the portion of the handle secured to the absorbent material preventing axial escape of the strand from the handle, the degree of containment of the strand in the tubular handle afforded by the wall construction of the handle and the associated axial escape prevention means being sufficient to effectively avoid the risk of separation of the indicating strand or a portion thereof from the handle resulting from breakage through excessive strain or embrittlement of said strand, the encapsulation of the strand of radiopaque material by the handle likewise protecting the radiopaque material from abrasion, snagging, and like harm during handling of the sponge.

2. A medical sponge as set forth in claim 1, wherein said handle is an elongated element and said radiopaque material is substantially coextensive with the length of the handle.

3. A medical sponge as set forth in claim 2, wherein said handle is a tube having a seamless wall structure.

4. A medical sponge as set forth in claim 3, wherein said tube is braided with threads, said threads being substantially contiguous, said radiopaque strand having a diameter substantially greater than the diameter of said threads.

5. A medical sponge as set forth in claim 4, wherein said threads are braided in a configuration sufficiently tight, with respect to the transverse cross section of the radiopaque strand, to prevent endwise escape of the strand through the wall of the tube handle.

6. A medical sponge as set forth in claim 2, wherein said handle has its ends attached with said absorbent material at a common point and a major portion of its length intermediate said ends forming a loop free of said absorbent material.

7. A medical sponge as set forth in claim 1, wherein said absorbent material is arranged in a generally rectangular or square sheet.

8. A medical sponge as set forth in claim 7, wherein said absorbent material sheet is a fabric of intertwined threads.

9. A medical sponge as set forth in claim 8, wherein said fabric sheet includes a folded hem, said handle being attached to said hem at an end thereof by stitches.

10. A medical sponge as set forth in claim 9, wherein said hem extends around the periphery of said sheet, said handle end being attached at a corner of said sheet.

11. A medical sponge as set forth in claim 10, wherein said handle end lies in a direction parallel to the hem to which it is stitched, and the remaining free length of the handle extends in a direction away from said sheet.

12. A medical sponge as set forth in claim 11, wherein said sheet has at least one ply of fabric, the hem of said corner having twice the number of plies as said sheet, said handle ends being disposed and anchored between the plies of the hem.

* * * * *